US006274134B1

(12) United States Patent
Beckner et al.

(10) Patent No.: US 6,274,134 B1
(45) Date of Patent: Aug. 14, 2001

(54) HUMAN CELL ADHESION PROTEIN AAMP-1 AND USES THEREOF

(75) Inventors: Marie E. Beckner; Henry C. Krutzsch, both of Bethesda; Lance A. Liotta, Potomac, all of MD (US)

(73) Assignee: National Institutes of Health, Rockville, MD (US)

( * ) Notice: Subject to any disclaimer, the term of this patent is extended or adjusted under 35 U.S.C. 154(b) by 0 days.

(21) Appl. No.: 08/083,945

(22) Filed: Jun. 25, 1993

Related U.S. Application Data

(63) Continuation-in-part of application No. 07/827,043, filed on Jan. 29, 1992, now abandoned.

(51) Int. Cl.[7] .............................. A61K 45/00; C07K 1/00; C07K 14/00; C07K 17/00
(52) U.S. Cl. ........................ 424/85.1; 530/350; 536/27.1
(58) Field of Search .................... 424/85.1, 88; 530/350; 435/172.2; 536/27

(56) References Cited

U.S. PATENT DOCUMENTS

| | | | |
|---|---|---|---|
| 4,839,464 | * 6/1989 | McCarthy | ............................. 530/326 |
| 4,870,160 | 9/1989 | Charonis . | |
| 5,081,031 | 1/1992 | Tsilibary . | |
| 5,110,906 | 5/1992 | Maddon . | |
| 5,120,828 | 6/1992 | Charonis . | |
| 5,126,433 | 6/1992 | Maddon . | |
| 5,152,784 | 10/1992 | Tsilibary . | |

FOREIGN PATENT DOCUMENTS

| | | |
|---|---|---|
| 01493 | 2/1989 | (WO) . |
| 01942 | 3/1989 | (WO) . |
| 13566 | 11/1990 | (WO) . |
| 09054 | 6/1991 | (WO) . |
| 09113 | 6/1991 | (WO) . |
| 12739 | 8/1992 | (WO) . |
| 15202 | 8/1993 | (WO) . |

OTHER PUBLICATIONS

Kurkinen, et al, 1984, "Cell Surface–Associated Proteins . . . " J. Biol. Chem. 259(9): 5915–5922.*
Edelman et al., "Cell Adhesion Molecules: Implications for a Molecular Histology," Ann Rev. Biochem. 60:155–90 (1991).
Edelman, G. M., "Morphoregulation," Dev. Dynamics 193:2–10 (1992).
Golding, et al., Identification of Homologous Regions in Human Immunodeficiency Virus I gp–41 and MHC Class II β I Domain, J. Exp. Med. 167:914–923 (1988).
Kallapur et al., "The Neural Cell Adhesion Molecule (NCAM) Heparin Binding Domain Binds to Cell Surface Heparan Sulfate Proteoglycans," J. Neurosci. Res. 33:538–548 (1992).

Levy et al., "Immunoglobulin–Sulfated Polysaccharide Interactions: Binding of Agaropectin and Heparin by Human IgG Proteins," J. Exp. Med. 153(4):883–96 (Apr. 1981).
Mooradian et al., "Rabbit Corneal Epithelial Cells Adhere to Two Distinct Heparin–Binding Synthetic Peptides Derived From Fibronectin," Invest. Opthamol. Vis. Sci. 33(11):3034–40 (Oct. 1992).
Rao et al., "Identification and Characterization of a 43–Kilodalton Laminin Fragment from the "A" Chain (Long Arm) with High–Affinity Heparin Binding and Mammary Epithelial Cell Adhesion–Spreading Activities," Biochemistry 29(29):6768–6777 (Jul. 24, 1990).
Reyes et al. "Structural Requirements for Neural Cell Adhesion Molecule–Heparin Interaction," Cell. Regul. 1(8):567–76 (Jun. 1990).
Beckner et al., "A New Monoclonal Antibody, 1AA3, Affects Generalized Motility In A2058 Melanoma Cells," J. Cellular Biochem. Supp. 14A, p. 175, Abstract A300 (1990).
Becker et al., "New Melanoma Protein 1AA335B With CD4 Similarity," J. Cell Biochem. Supp. 16B, 311 (1992).
Behrens et al., "Cell Adhesion in Invasion and Metastasis," Sem. Cell Biol. 3:169–78 (1992).
Clarke, M. F., et al. "Homology of Human T–cell Leukemia Virus Envelope Gene with Class I HLA Gene," Nature 305:60–62 (1983).
Skubitz et al., "Synthetic Peptides From the Carboxy–Terminal Globular Domain of the A–Chain of Laminin: Their Ability to Promote Cell Adhesion and Neurite Outgrowth, and Interact with Heparin and the Beta–I–Integrin Subunit," J. Cell Biol. 115:1137–48 (Nov. 1991).
Vega et al., "Autoimmune Response in AIDS," Nature 345:26 (1990).
Wilke et al., "Human Keratinocytes Adhere to Two Distinct Heparin–Binding Synthetic Peptides Derived from Fibronectin," J. Invest. Derm. 97:573–79 (Sep. 1991).

* cited by examiner

Primary Examiner—Brett L. Nelson
(74) Attorney, Agent, or Firm—Townsend and Townsend and Crew LLP

(57) ABSTRACT

The present invention relates, in general, to AAMP-1, and to a peptide derived from the amino-terminal region of AAMP, P189. In particular, the present invention relates to a DNA segment encoding AAMP-1, P189 or fragments thereof; polypeptides encoded by said DNA segment; recombinant DNA molecules containing the DNA segment; cells containing the recombinant DNA molecule; a method of producing a AAMP-1, and P189 polypeptide or fragments thereof; antibodies specific to AAMP-1; and a method of measuring the amount of AAMP-1 in a sample. The present invention further relates to methods of using AAMP, P189 or fragments thereof in promoting cell-cell or cell-substrate adhesion, wound healing in patients, prosthetic acceptance, concentrating heparin in tissues, and inhibiting metastases and invasion of malignant cells.

4 Claims, 6 Drawing Sheets

```
gggcccagagaagtggatccgccgcttgcgccgcatggagtccgaatcggaaagcggggct    61
  G  P  E  K  W  I  R  R  L  R  R  M  E  S  E  S  E  S  G  A    20 gctgctgacacccccactggagaccctaagcttccatggtgatgaagagattatcgag     121
 A  A  D  T  P  P  L  E  T  L  S  F  H  G  D  E  E  I  I  E    40
                                              - - - - - - - - gtggtagaacttgatcccggtccgccggacccagatgacctggcccaggagatggaagat   181
 V  V  E  L  D  P  G  P  P  D  P  D  D  L  A  Q  E  M  E  D    60
- - - - - - - - - - - - - - - - - - - - - - - - - - - - - - gtggactttgaggaagaagaggaggaagagggcaacgaagagggctgggttctagaaccc   241
 V  D  F  E  E  E  E  E  E  G  N  E  E  G  W  V  L  E  P       80
- - - - - - - - - - - - - - - - - - - - - - - - - - caggaaggggtggtcggcagcatggagggccccgacgatagcgaggtcacctttgcattg   301
 Q  E  G  V  V  G  S  M  E  G  P  D  D  S  E  V  T  F  A  L   100
- - - -                 > > > > > > >     * * * * * * cactcagcatctgtgttttgtgtgagcctggaccccaagaccaataccttggcagtgacc   361
 H  S  A  S  V  F <C> V  S  L  D  P  K  T  N  T  L  A  V  T   120
                   * * * * * *       >       * * * * * * * * ggggggtgaagatgacaaagccttcgtatggcggctcagcgatggggagctgctctttgag  421
 G  G  E  D  D  K  A  F  V [W  R] L  S  D  G  E  L  L  F  E   140
 > > > > > > >       * * * * * *       > > >     * * * * * * tgtgcaggccataaagactctgtgacttgtgctggtttcagccatgactccactctagtg   481
<C> A  G  H  K  D  S  V  T <C> A  G  F  S  H  D  S  T  L  V   160
 *                 >         * * * * * * * *       >  * * * * gccacaggggacatgagtggcctcttgaaagtgtggcaggtggacactaaggaggaggtc   541
 A  T  G  D  M  S  G  L  L  K  V [W  Q] V  D  T  K  E  E  V   180
 * * * * * * * * * * * * * * * * *       >     * tggtccttgaagcgggagacctggagtggatggagtggcatcctcgggcacctgtcctg   601
 W  S  F  E  A  G  D  L  E  W  M  E  W  H  P  R  A  P  V  L   200
 * * * * *                 * * * * * * *       >     * * * ttggcgggcacagctgacggcaacacctggatgtggaaagtcccgaatggtgactgcaag   661
 L  A  G  T  A  D  G  N  T  W  M  W  K  V  P  N  G <C> K      220
 * * * * *         > > >     * * * * * * *       > > >   * * * accttccagggtcccaactgcccagccacctgtggccgagtcctccctgatgggaagaga   721
 T  F  Q  G  P  N <C> P  A  T  C  G  R  V  L  P  D  G  K  R   240
 * * * *       > > >     * * * * * * * * * * *       > > > > gctgtggtaggctatgaagatgggaccatcaggatttgggacctgaagcagggaagccct   781
 A  V  V  G  Y  E  D  G  T  I  R  I [W  D] L  K  Q  G  S  P   260
 * * * *       > > >     * * * * * * * * *     * *   > > > atccatgtactgaaagggactgagggtcaccagggcccactcacctgtgttgctgccaac   841
 I  H  V  L  K  G  T  E  G  H  Q  G  P  L  T <C> V  A  A  N   280
 * * * * * * * * *           * * * * * * * caggatggcagcttgatcctaactggctctgtggactgccaggccaagctggtcagtgcc   901
 Q  D  G  S  L  I  L  T  G  S  V  D <C> Q  A  K  L  V  S  A   300
 > > > >     * * * * * * * * * * * * * * * * * * * * * * * accaccggcaaggtggtgggtgtttttagacctgagactgtggcctcccagcccagcctg   961
 T  T  G  K  V  V  G  V  F  R  P  E  T  V  A  S  Q  P  S  L   320
 * * * * * * * * * * * * * * * * * * * * * * *   *   >
                                      <           < ggagaaggggaggagagtgagtccaactcggtggagtccttgggcttctgcagtgtgatg  1021
 G  E  G  E  E  S  E  S  N  S  V  E  S  L  G  F <C> S  V  M   340
 > > > > > > > > > > > > >             * * * * * * * * cccctggcagctgttggctacctggatgggaccttggccatctatgacctggctacgcag  1081
 P  L  A  A  V  G  Y  L  D  G  T  L  A  I [Y  D] L  A  T  Q   360
 * * * * * * * * * * * * * * * * * *   * * * * actcttaggcatcagtgtcagcaccagtcgggcatcgtgcagctgctgtgggaggcaggc  1141
 T  L  R  H  Q  C  Q  H  Q  S  G  I  V  Q  L  L  W  E  A  G   380
```

FIG. 1A

```
actgccgtggtatataccctgcagcctggatggcatcgtgcgcctctgggacgcccggacc 1201
  T   A   V   V   Y   T   C   S   L   D   G   I   V   R   L  [W   D]  A   R   T    400
                                                  - - - - - - - - - - - - ggccgcctgcttactgactaccggggccacacggctgagatcctggactttgccctcagc 1261
  G   R   L   L   T   D   Y   R   G   H   T   A   E   I   L   D   F   A   L   S    420
  - - - - - - - - - aaagatgcctccctggtggtgaccacgtcaggagaccacaaagcgaaagtattttgtgtc 1321
  K   D   A   S   L   V   V   T   T   S   G   D   H   K   A   K   V   F   C   V    440 caaaggcctgaccgttaatggctgcagcccctgcctgtgtgtctggtgttgaggggacga 1381
  Q   R   P   D   R   -                                                              445 agggacccctgccctgtctgccagcagaggcagtagggcacagagggaagaggagggtg 1441
ggccctggatgactttccagcctcttcaactgacttgctcccctctccttttcttctct 1501
ttagagacccagcccagggccctccacccttgcccagacctggtgggcccttcagaggg 1561
aggggtggacctgtttctcttcactttcatttgctggtgtgagccatggggtgtgtatt 1621
tgtatgtggggagtaggtgtttgaggttcccgttctttcccttcccaagtctctgggggt 1681
ggaaggaggaagagatactagttaaagattttaaaaatgta(aataaaa)tatacttccca 1741
gaaaaaaaaaaaaaaaaaaaaaaaaa
```

FIG. 1B

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 1767 base pairs
        (B) TYPE: nucleic acid
        (C) STRANDEDNESS: single
        (D) TOPOLOGY: linear (ii) MOLECULE TYPE: c-DNA (ix) FEATURE:
        (A) NAME/KEY: CDS
        (B) LOCATION: 2..1336

(xi) SEQUENCE DESCRIPTION: SEQ ID NO:1:

```
G GGC CCA GAG AAG TGG ATC CGC CGC TTG CGC CGC ATG GAG TCC GAA TCG      49
  Gly Pro Glu Lys Trp Ile Arg Arg Leu Arg Arg Met Glu Ser Glu Ser
  1               5                  10                  15

GAA AGC GGG GCT GCT GCT GAC ACC CCC CCA CTG GAG ACC CTA AGC TTC        97
Glu Ser Gly Ala Ala Ala Asp Thr Pro Pro Leu Glu Thr Leu Ser Phe
             20                  25                  30

CAT GGT GAT GAA GAG ATT ATC GAG GTG GTA GAA CTT GAT CCC GGT CCG        145
His Gly Asp Glu Glu Ile Ile Glu Val Val Glu Leu Asp Pro Gly Pro
         35                  40                  45

CCG GAC CCA GAT GAC CTG GCC CAG GAG ATG GAA GAT GTG GAC TTT GAG        193
Pro Asp Pro Asp Asp Leu Ala Gln Glu Met Glu Asp Val Asp Phe Glu
     50                  55                  60

GAA GAA GAG GAG GAA GAG GGC AAC GAA GAG GGC TGG GTT CTA GAA CCC        241
Glu Glu Glu Glu Glu Glu Gly Asn Glu Glu Gly Trp Val Leu Glu Pro
 65                  70                  75                  80

CAG GAA GGG GTG GTC GGC AGC ATG GAG GGC CCC GAC GAT AGC GAG GTC        289
Gln Glu Gly Val Val Gly Ser Met Glu Gly Pro Asp Asp Ser Glu Val
                 85                  90                  95

ACC TTT GCA TTG CAC TCA GCA TCT GTG TTT TGT GTG AGC CTG GAC CCC        337
Thr Phe Ala Leu His Ser Ala Ser Val Phe Cys Val Ser Leu Asp Pro
             100                 105                 110

AAG ACC AAT ACC TTG GCA GTG ACC GGG GGT GAA GAT GAC AAA GCC TTC        385
Lys Thr Asn Thr Leu Ala Val Thr Gly Gly Glu Asp Asp Lys Ala Phe
         115                 120                 125

GTA TGG CGG CTC AGC GAT GGG GAG CTG CTC TTT GAG TGT GCA GGC CAT        433
Val Trp Arg Leu Ser Asp Gly Glu Leu Leu Phe Glu Cys Ala Gly His
     130                 135                 140

AAA GAC TCT GTG ACT TGT GCT GGT TTC AGC CAT GAC TCC ACT CTA GTG        481
Lys Asp Ser Val Thr Cys Ala Gly Phe Ser His Asp Ser Thr Leu Val
145                 150                 155                 160

GCC ACA GGG GAC ATG AGT GGC CTC TTG AAA GTG TGG CAG GTG GAC ACT        529
Ala Thr Gly Asp Met Ser Gly Leu Leu Lys Val Trp Gln Val Asp Thr
                 165                 170                 175

AAG GAG GAG GTC TGG TCC TTT GAA GCG GGA GAC CTG GAG TGG ATG GAG        577
```

```
Lys Glu Glu Val Trp Ser Phe Glu Ala Gly Asp Leu Glu Trp Met Glu
            180                 185                 190

TGG CAT CCT CGG GCA CCT GTC CTG TTG GCG GGC ACA GCT GAC GGC AAC         625
Trp His Pro Arg Ala Pro Val Leu Leu Ala Gly Thr Ala Asp Gly Asn
        195                 200                 205

ACC TGG ATG TGG AAA GTC CCG AAT GGT GAC TGC AAG ACC TTC CAG GGT         673
Thr Trp Met Trp Lys Val Pro Asn Gly Asp Cys Lys Thr Phe Gln Gly
    210                 215                 220

CCC AAC TGC CCA GCC ACC TGT GGC CGA GTC CTC CCT GAT GGG AAG AGA         721
Pro Asn Cys Pro Ala Thr Cys Gly Arg Val Leu Pro Asp Gly Lys Arg
225                 230                 235                 240

GCT GTG GTA GGC TAT GAA GAT GGG ACC ATC AGG ATT TGG GAC CTG AAG         769
Ala Val Val Gly Tyr Glu Asp Gly Thr Ile Arg Ile Trp Asp Leu Lys
                245                 250                 255

CAG GGA AGC CCT ATC CAT GTA CTG AAA GGG ACT GAG GGT CAC CAG GGC         817
Gln Gly Ser Pro Ile His Val Leu Lys Gly Thr Glu Gly His Gln Gly
            260                 265                 270

CCA CTC ACC TGT GTT GCT GCC AAC CAG GAT GGC AGC TTG ATC CTA ACT         865
Pro Leu Thr Cys Val Ala Ala Asn Gln Asp Gly Ser Leu Ile Leu Thr
        275                 280                 285

GGC TCT GTG GAC TGC CAG GCC AAG CTG GTC AGT GCC ACC ACC GGC AAG         913
Gly Ser Val Asp Cys Gln Ala Lys Leu Val Ser Ala Thr Thr Gly Lys
    290                 295                 300

GTG GTG GGT GTT TTT AGA CCT GAG ACT GTG GCC TCC CAG CCC AGC CTG         961
Val Val Gly Val Phe Arg Pro Glu Thr Val Ala Ser Gln Pro Ser Leu
305                 310                 315                 320

GGA GAA GGG GAG GAG AGT GAG TCC AAC TCG GTG GAG TCC TTG GGC TTC        1009
Gly Glu Gly Glu Glu Ser Glu Ser Asn Ser Val Glu Ser Leu Gly Phe
                325                 330                 335

TGC AGT GTG ATG CCC CTG GCA GCT GTT GGC TAC CTG GAT GGG ACC TTG        1057
Cys Ser Val Met Pro Leu Ala Ala Val Gly Tyr Leu Asp Gly Thr Leu
            340                 345                 350

GCC ATC TAT GAC CTG GCT ACG CAG ACT CTT AGG CAT CAG TGT CAG CAC        1105
Ala Ile Tyr Asp Leu Ala Thr Gln Thr Leu Arg His Gln Cys Gln His
        355                 360                 365

CAG TCG GGC ATC GTG CAG CTG CTG TGG GAG GCA GGC ACT GCC GTG GTA        1153
Gln Ser Gly Ile Val Gln Leu Leu Trp Glu Ala Gly Thr Ala Val Val
    370                 375                 380

TAT ACC TGC AGC CTG GAT GGC ATC GTG CGC CTC TGG GAC GCC CGG ACC        1201
Tyr Thr Cys Ser Leu Asp Gly Ile Val Arg Leu Trp Asp Ala Arg Thr
385                 390                 395                 400

GGC CGC CTG CTT ACT GAC TAC CGG GGC CAC ACG GCT GAG ATC CTG GAC        1249
Gly Arg Leu Leu Thr Asp Tyr Arg Gly His Thr Ala Glu Ile Leu Asp
                405                 410                 415

TTT GCC CTC AGC AAA GAT GCC TCC CTG GTG GTG ACC ACG TCA GGA GAC        1297
Phe Ala Leu Ser Lys Asp Ala Ser Leu Val Val Thr Thr Ser Gly Asp
            420                 425                 430

CAC AAA GCG AAA GTA TTT TGT GTC CAA AGG CCT GAC CGT TAATGGCTGC        1346
His Lys Ala Lys Val Phe Cys Val Gln Arg Pro Asp Arg
        435                 440                 445

AGCCCCTGCC TGTGTGTCTG GTGTTGAGGG GACGAAGGGA CCCCTGCCCC TGTCTGCCAG     1406

CAGAGGCAGT AGGGCACAGA GGGAAGAGGA GGGTGGGGCC CTGGATGACT TTCCAGCCTC     1466

TTCAACTGAC TTGCTCCCCT CTCCTTTTCT TCTCTTTAGA GACCCAGCCC AGGGCCCTCC     1526

CACCCTTGCC CAGACCTGGT GGGCCCTTCA GAGGGAGGGG TGGACCTGTT TCTCTTTCAC     1586

TTTCATTTGC TGGTGTGAGC CATGGGGTGT GTATTTGTAT GTGGGGAGTA GGTGTTTGAG     1646

GTTCCCGTTC TTTCCCTTCC CAAGTCTCTG GGGGTGGAAA GGAGGAAGAG ATACTAGTTA     1706
```

-continued

```
AAGATTTTAA AAATGTAAAT AAAATATACT TCCCAGAAAA AAAAAAAAAA AAAAAAAAA    1766
A                                                                   1767
```

(2) INFORMATION FOR SEQ ID NO:2:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO:2:

```
Gly Pro Glu Lys Trp Ile Arg Arg Leu Arg Arg Met Glu Ser Glu Ser
 1               5                  10                  15

Glu Ser Gly Ala Ala Ala Asp Thr Pro Pro Leu Glu Thr Leu Ser Phe
            20                  25                  30

His Gly Asp Glu Glu Ile Ile Glu Val Val Glu Leu Asp Pro Gly Pro
        35                  40                  45

Pro Asp Pro Asp Asp Leu Ala Gln Glu Met Glu Asp Val Asp Phe Glu
    50                  55                  60

Glu Glu Glu Glu Glu Glu Gly Asn Glu Glu Gly Trp Val Leu Glu Pro
65                  70                  75                  80

Gln Glu Gly Val Val Gly Ser Met Glu Gly Pro Asp Asp Ser Glu Val
                85                  90                  95

Thr Phe Ala Leu His Ser Ala Ser Val Phe Cys Val Ser Leu Asp Pro
            100                 105                 110

Lys Thr Asn Thr Leu Ala Val Thr Gly Gly Glu Asp Asp Lys Ala Phe
        115                 120                 125

Val Trp Arg Leu Ser Asp Gly Glu Leu Leu Phe Glu Cys Ala Gly His
    130                 135                 140

Lys Asp Ser Val Thr Cys Ala Gly Phe Ser His Asp Ser Thr Leu Val
145                 150                 155                 160

Ala Thr Gly Asp Met Ser Gly Leu Leu Lys Val Trp Gln Val Asp Thr
                165                 170                 175

Lys Glu Glu Val Trp Ser Phe Glu Ala Gly Asp Leu Glu Trp Met Glu
            180                 185                 190

Trp His Pro Arg Ala Pro Val Leu Leu Ala Gly Thr Ala Asp Gly Asn
        195                 200                 205

Thr Trp Met Trp Lys Val Pro Asn Gly Asp Cys Lys Thr Phe Gln Gly
    210                 215                 220

Pro Asn Cys Pro Ala Thr Cys Gly Arg Val Leu Pro Asp Gly Lys Arg
225                 230                 235                 240

Ala Val Val Gly Tyr Glu Asp Gly Thr Ile Arg Ile Trp Asp Leu Lys
                245                 250                 255

Gln Gly Ser Pro Ile His Val Leu Lys Gly Thr Glu Gly His Gln Gly
            260                 265                 270

Pro Leu Thr Cys Val Ala Ala Asn Gln Asp Gly Ser Leu Ile Leu Thr
        275                 280                 285

Gly Ser Val Asp Cys Gln Ala Lys Leu Val Ser Ala Thr Thr Gly Lys
    290                 295                 300

Val Val Gly Val Phe Arg Pro Glu Thr Val Ala Ser Gln Pro Ser Leu
305                 310                 315                 320

Gly Glu Gly Glu Glu Ser Glu Ser Asn Ser Val Glu Ser Leu Gly Phe
                325                 330                 335
```

```
Cys Ser Val Met Pro Leu Ala Ala Val Gly Tyr Leu Asp Gly Thr Leu
            340                 345                 350

Ala Ile Tyr Asp Leu Ala Thr Gln Thr Leu Arg His Gln Cys Gln His
            355                 360                 365

Gln Ser Gly Ile Val Gln Leu Leu Trp Glu Ala Gly Thr Ala Val Val
            370                 375                 380

Tyr Thr Cys Ser Leu Asp Gly Ile Val Arg Leu Trp Asp Ala Arg Thr
385                 390                 395                 400

Gly Arg Leu Leu Thr Asp Tyr Arg Gly His Thr Ala Glu Ile Leu Asp
                405                 410                 415

Phe Ala Leu Ser Lys Asp Ala Ser Leu Val Val Thr Thr Ser Gly Asp
                420                 425                 430

His Lys Ala Lys Val Phe Cys Val Gln Arg Pro Asp Arg
                435                 440                 445

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..36

(xi) SEQUENCE DESCRIPTION: SEQ ID NO:3:

CGC CGC TTG CGC CGC ATG GAG TCC GAA TCG GAA AGC                     36
Arg Arg Leu Arg Arg Met Glu Ser Glu Ser Glu Ser
 1               5                  10

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:4:

Arg Arg Leu Arg Arg Met Glu Ser Glu Ser Glu Ser
 1               5                  10

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:5:

CGC CGC TTG CGC CGC ATG                                             18
Arg Arg Leu Arg Arg Met
 1               5
```

(2) INFORMATION FOR SEQ ID NO:6:

(i) SEQUENCE CHARACTERISTICS:
      (A) LENGTH: 6 amino acids
      (B) TYPE: amino acid
      (D) TOPOLOGY: linear (ii) MOLECULE TYPE: protein (xi) SEQUENCE DESCRIPTION: SEQ ID NO:6:

Arg Arg Leu Arg Arg Met
 1               5

(2) INFORMATION FOR SEQ ID NO:7:

(i) SEQUENCE CHARACTERISTICS:
      (A) LENGTH: 445 amino acids
      (B) TYPE: amino acid
      (D) TOPOLOGY: linear (ii) MOLECULE TYPE: protein (xi) SEQUENCE DESCRIPTION: SEQ ID NO:7:

Gly Pro Glu Lys Trp Ile Arg Arg Leu Arg Arg Met Glu Ser Glu Ser
 1               5                  10                  15

Glu Ser Gly Ala Ala Ala Asp Thr Pro Pro Leu Glu Thr Leu Ser Phe
            20                  25                  30

His Gly Asp Glu Glu Ile Ile Glu Val Val Glu Leu Asp Pro Gly Pro
        35                  40                  45

Pro Asp Pro Asp Asp Leu Ala Gln Glu Met Glu Asp Val Asp Phe Glu
    50                  55                  60

Glu Glu Glu Glu Glu Gly Asn Glu Glu Gly Trp Val Leu Glu Pro
65                  70                  75                  80

Gln Glu Gly Val Val Gly Ser Met Glu Gly Pro Asp Asp Ser Glu Val
                85                  90                  95

Thr Phe Ala Leu His Ser Ala Ser Val Phe Cys Val Ser Leu Asp Pro
            100                 105                 110

Lys Thr Asn Thr Leu Ala Val Thr Gly Gly Glu Asp Asp Lys Ala Phe
        115                 120                 125

Val Trp Arg Leu Ser Asp Gly Glu Leu Leu Phe Glu Cys Ala Gly His
    130                 135                 140

Lys Asp Ser Val Thr Cys Ala Gly Phe Ser His Asp Ser Thr Leu Val
145                 150                 155                 160

Ala Thr Gly Asp Met Ser Gly Leu Leu Lys Val Trp Gln Val Asp Thr
                165                 170                 175

Lys Glu Glu Val Trp Ser Phe Glu Ala Gly Asp Leu Glu Trp Met Glu
            180                 185                 190

Trp His Pro Arg Ala Pro Val Leu Leu Ala Gly Thr Ala Asp Gly Asn
        195                 200                 205

Thr Trp Met Trp Lys Val Pro Asn Gly Asp Cys Lys Thr Phe Gln Gly
    210                 215                 220

Pro Asn Cys Pro Ala Thr Cys Gly Arg Val Leu Pro Asp Gly Lys Arg
225                 230                 235                 240

Ala Val Val Gly Tyr Glu Asp Gly Thr Ile Arg Ile Trp Asp Leu Lys
                245                 250                 255

Gln Gly Ser Pro Ile His Val Leu Lys Gly Thr Glu Gly His Gln Gly
            260                 265                 270

Pro Leu Thr Cys Val Ala Ala Asn Gln Asp Gly Ser Leu Ile Leu Thr
        275                 280                 285

```
Gly Ser Val Asp Cys Gln Ala Lys Leu Val Ser Ala Thr Thr Gly Lys
    290                 295                 300
Val Val Gly Val Phe Arg Pro Glu Thr Val Ala Ser Gln Pro Ser Leu
305                 310                 315                 320
Gly Glu Gly Glu Glu Ser Glu Ser Asn Ser Val Glu Ser Leu Gly Phe
                325                 330                 335
Cys Ser Val Met Pro Leu Ala Ala Val Gly Tyr Leu Asp Gly Thr Leu
            340                 345                 350
Ala Ile Tyr Asp Leu Ala Thr Gln Thr Leu Arg His Gln Cys Gln His
        355                 360                 365
Gln Ser Gly Ile Val Gln Leu Leu Trp Glu Ala Gly Thr Ala Val Val
    370                 375                 380
Tyr Thr Cys Ser Leu Asp Gly Ile Val Arg Leu Trp Asp Ala Arg Thr
385                 390                 395                 400
Gly Arg Leu Leu Thr Asp Tyr Arg Gly His Thr Ala Glu Ile Leu Asp
                405                 410                 415
Phe Ala Leu Ser Lys Asp Ala Ser Leu Val Val Thr Thr Ser Gly Asp
            420                 425                 430
His Lys Ala Lys Val Phe Cys Val Gln Arg Pro Asp Arg
        435                 440                 445

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGGAGGAAGA G                                                              11

(2) INFORMATION FOR SEQ ID NO:9:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGGTTCTAGA ACCC                                                           14

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:10:

Met Ser Arg Glu Arg Glu Ser Arg Glu Arg Ser Leu
1               5                   10

(2) INFORMATION FOR SEQ ID NO:11:
```

(i) SEQUENCE CHARACTERISTICS:
            (A) LENGTH: 12 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:11:

Gln Gln Leu Gln Gln Met Glu Ser Glu Ser Glu Ser
1               5                   10

(2) INFORMATION FOR SEQ ID NO:12:

(i) SEQUENCE CHARACTERISTICS:
            (A) LENGTH: 12 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:12:

Arg Arg Leu Arg Arg Met Gln Ser Gln Ser Gln Ser
1               5                   10

(2) INFORMATION FOR SEQ ID NO:13:

(i) SEQUENCE CHARACTERISTICS:
            (A) LENGTH: 12 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:13:

Arg Arg Gly Arg Arg Gly Glu Ser Glu Ser Glu Ser
1               5                   10

(2) INFORMATION FOR SEQ ID NO:14:

(i) SEQUENCE CHARACTERISTICS:
            (A) LENGTH: 12 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:14:

Arg Arg Leu Arg Arg Met Glu Ala Glu Ala Glu Ala
1               5                   10

(2) INFORMATION FOR SEQ ID NO:15:

(i) SEQUENCE CHARACTERISTICS:
            (A) LENGTH: 10 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:15:

Arg Leu Arg Arg Met Glu Ser Glu Ser Glu
1               5                   10

HUMAN CELL ADHESION PROTEIN AAMP-1 AND USES THEREOF

This is a continuation-in-part application of U.S. Ser. No. 07/827,043, filed Jan. 29, 1992 (now abandoned), which is hereby incorporated by reference and benefit is claimed of its filing date.

BACKGROUND OF THE INVENTION

1. Field of the Invention

The present invention relates, in general, to AAMP-1, and to a peptide derived from the amino-terminal region of AAMP, P189. In particular, the present invention relates to a DNA segment encoding AAMP-1, P189 or fragments thereof; polypeptides encoded by the DNA segments; recombinant DNA molecules containing the DNA segments; cells containing the recombinant DNA molecule; a method of producing AAMP-1, P189 or fragments thereof; antibodies specific to AAMP-1; and a method of measuring the amount of AAMP-1 in a sample. The present invention further relates to methods of using AAMP, P189 or fragments thereof in promoting cell-cell or cell-substrate adhesion, wound healing in patients, prosthetic acceptance, concentrating heparin in tissues, and inhibiting metastases and invasion of malignant cells.

2. Background Information

The major histocompatibility complex class II proteins have recently been found to contain local homologies to the HIV-1 envelope protein (H. Golding et al., *J. Exp. Med.* 167, 914 (1988); H. Golding et al., *J. Clin. Invest.* 83, 1430 (1989); J. A. T. Young, *Nature* 332, 215 (1988)). Such homologous regions may serve as targets for antibodies generated to HIV-1 proteins and thus compromise the immune system in AIDS. Golding et al. (*J. Exp. Med.* 167, 914 (1988)) have identified a common epitope located in the carboxy terminus of the HIV-1 gp4l-envelope protein and the amino terminal portion of the beta chain of all human HLA class II antigens. Although the epitope is small, 5 consecutive identities or similarities, they found that it is an effective example of "molecular mimicry" in that monoclonal antibodies raised against synthetic peptides from each protein react interchangeably with native HIV-1 envelope and MHC class II molecules. One third of HIV-1 positive individuals were shown to have serum antibodies directed against peptides derived from HIV-1 envelope protein, the homologous peptide from the MHC class II molecules, and native MHC class II molecules (H. Golding et al. *J. Exp. Med.* 167, 914 (1988)). Two other regions of the HLA class II beta chain and another immune related protein, interleukin-2, also show limited homology to HIV-1 (J. A. T. Young, *Nature* 333:215 (1988); M. A. Vega et al. *Nature* 345:26 (1990); W. E. Reiher III, et al. *Proc. Natl. Acad. Sci. USA* 83:9188 (1986)). An important consideration in HIV-1 vaccine development is the potential existence of additional host cell surface proteins with homologies to HIV-1 that may cross-react with antibodies directed against its peptides.

Certain adhesive molecules are known to carry out cell-cell and cell-substrate interactions which play a central role in development, differentiation, immune functions, wound healing, malignant transformation, and tumor invasion metastasis. They provide structural patterns in tissue architecture, participate in transmembrane links between the cytoskeleton and the extracellular matrix, serve as directional guides for migrating cells, participate in signal transduction, provide strong adhesion that may inhibit cell motility, or alternatively, weak and/or reversible adhesion that provides traction in cell motility (Edelman, G. M. Ann. Rev. Cell Biol. 2:81–116 (1986); Edelman et al. Ann. Rev. Biochem. 60:155–90 (1991); Edelman, G. M., Dev. Dynamics 193:2–10 (1992); Behrens, J., et al., Sem Cell Biol. 3:169–78 (1992).

Members of the Immunoglobulin superfamily are known to exhibit diverse binding properties, and include many adhesive proteins. Modulation of such adhesive proteins has been shown to play stimulatory or inhibitory roles in normal and tumor cell migration via alterations in intercellular adhesion, cell to substratum adhesion, and adherence of tumor cells and leukocytes to endothelial cells (Buck, C. A., Sem. Cell Biol. 3:179–88 (1992); Shevach, E. M. Immunophysiology, The Role of Cells and Cytokines in Immunity and Inflamation (Oppenheim, J. J., and Shevach, E. M., eds.) pp.104–28, Oxford University Press, New York). Furthermore, heparin and hyaluronan, two glycosaminoglycans, are known to be involved with the binding mechanisms of some of these adhesive proteins, such as Neural Cell Adhesion Molecule (NCAM), and the Cluster Differentiation (CD) proteins, CD4 and CD44. See, e.g., Buck, C. A., Sem. Cell Biol. 3:179–88 (1992); Cole, G. J. et al., Nature 320:445–7 (1986); Cole, G. J. et al., Neuron 2:1157–65 (1989); Reyes et al., Cell Regul. 1:567–76 (1990); Arufo et al., Cell 61:1303–13 (1990); Miyake et al., J. Exp. Med. 172:69–75 (1990); and Lederman, S. et al., J. Immunol. 143:1149–54 (1989).

The use of heparin binding proteins and peptides to promote heparin binding to synthetic substrates, cell adhesion to culture substrata, implant acceptance, and wound healing, as well as their use in inhibiting tumor metastasis and malignant cell invasion, has been previously described. (U.S. Pat. No. 5,081,031 to Furcht et al., U.S. Pat. No. 5,152,784, to Tsilibary et al., U.S. Pat. No. 5,120,828, to Charonis).

SUMMARY OF THE INVENTION

The present invention relates to the protein AAMP-1 which has immunoglobulin (Ig) type domains that contain strong local homologies to conserved regions of the HIV-1 envelope and nef proteins. The invention further relates to polypeptide, P189, derived from the amino terminal region of AAMP. Both P189 and AAMP are capable of promoting cell aggregation, and heparin binding.

It is a general object of this invention to provide AAMP-1 or a fragment thereof.

It is a specific object of this invention to provide a DNA segment which encodes AAMP-1, or a fragment thereof.

It is a further object of the invention to provide a polypeptide corresponding to a AAMP-1 gene, or a fragment thereof.

It is another object of the invention to provide a recombinant DNA molecule comprising a vector and a DNA segment encoding a AAMP-1 gene, or a segment thereof.

It is a further object of the invention to provide a cell that contains the above-described recombinant molecule.

It is another object of the invention to provide a method of producing the polypeptide, or its fragments, encoded for by the AAMP-1 gene, or segments thereof.

It is a further object of the invention to provide antibodies having binding affinity for AAMP-1, or a unique fragment thereof.

It is a further object of the invention to provide a method of measuring the amount of AAMP-1, or its fragments, in a sample.

It is another object of the invention to provide a therapeutic modality comprising the above-described polypeptides in an amount effective to elicit protective antibodies, block harmful auto-antibodies, or compete for HIV binding to body cells in a patient to the AIDS virus and a pharmaceutically acceptable diluent, carrier, or excipient.

It is also an object of the invention to provide P189 peptide or a fragment thereof.

It is a further object of the invention to provide a DNA segment encoding the P189 peptide or a fragment thereof.

It is an additional object of this invention to provide a method for mediating cell-cell and cell-substrate adhesion comprising the use of AAMP or a related heparin binding peptide.

It is also an object of this invention to provide methods for promoting cellular attachment to culture substrata, prosthetic acceptance, and wound healing, and for inhibiting metastasis and invasion by malignant cells, wherein said methods comprise the use of AAMP or its related heparin binding peptides.

Further objects and advantages of the present invention will be clear from the description that follows.

BRIEF DESCRIPTION OF THE DRAWINGS

FIGS. 1A and 1B. Nucleotide sequence of human A2058 melanoma cell AAMP-1 cDNA isolated from a lambda gt11 expression library with its predicted amino acid sequence. The phage insert, AAMP-1, was subcloned into Bluescript plasmid (Stratagene) for production of double stranded cDNA for sequencing using the dideoxynucleotide termination method (F. Sanger et al. *Proc. Natl. Acad. Sci. USA* 74, 5463 (1977)) with Sequenase 2.0 (U.S. Biochemical). Nucleotide residues are numbered beginning at the 5' end. Amino acid sequence numbering begins with the first amino acid residue (underlined with "=") of the open reading frame. The putative heparin binding site includes amino acid residues (aa) 7–12. The amino terminal acidic region, aa35–95, is underlined with "----". Amino acid region, 90–357, comprised of potential immunoglobulin-like domains (A. F. Williams and A. N. Barclay, *Ann Rev. Immunol.* 6, 381 (1988); A. F. Williams and A. N. Barclay, in *Immunoglobulin Genes*. T. Honjo et al. Eds. (Academic Press Limited, San Diego, Calif., 1989), pp. 361–387)) is underlined with secondary structure predications of beta strands, "****", and beta turns, ">>>>", based on the method of Chou and Fasman (*Advances in Enz.* 47, 45 (1978)). Cysteine pairs, 107 & 141, 150 & 219, 227 & 276, and 293 and 337, predicted by immunoglobulin domain homology to most likely form disulfide bonds are marked "<>". The potential transmembrane region, aa385–410, is underlined, "—". The polyadenylation site at nucleic acid residues, 1722–1728 is in parentheses "( )".

DETAILED DESCRIPTION OF THE INVENTION

Figure 2:
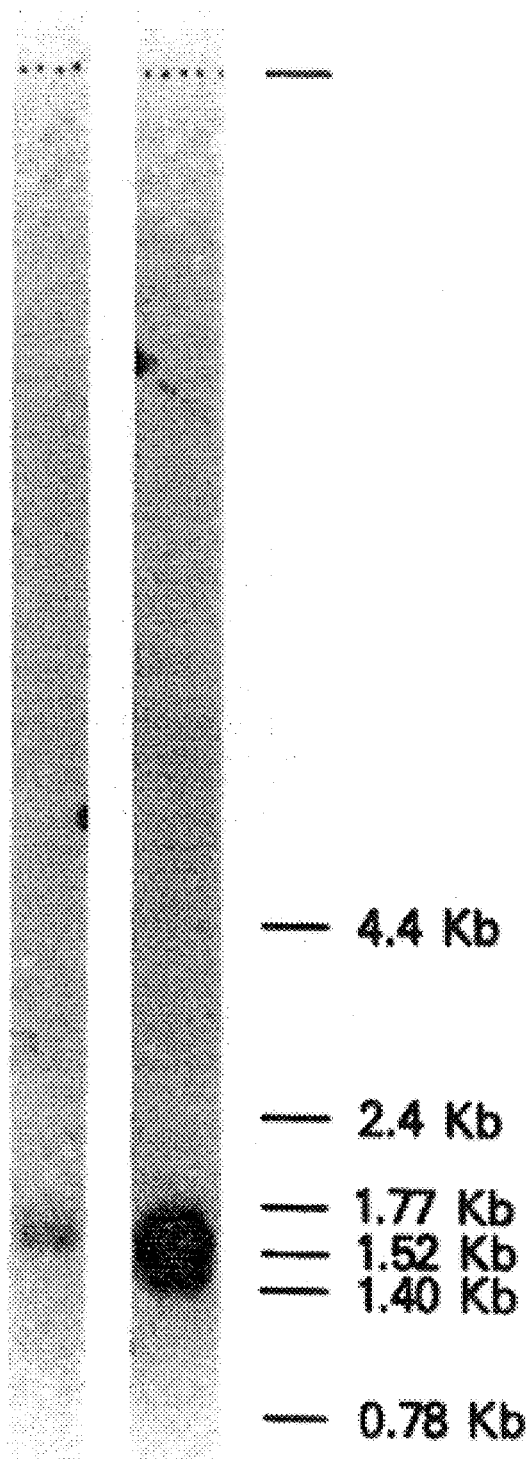
FIG. 2. Northern blot of human melanoma A2058 cells probed with AAMP-1 cDNA. A single 1.6Kb band is seen on blots of total cytoplasmic (Lane 1) and polyadenylate-enriched (Lane 2) A2058 RNA. Total cytoplasmic RNA, 41 micrograms ($\mu$g), was isolated from 6 million cells lysed in Nonidet P-40 (0.65%), separated into an aqueous phase in the presence of 7M urea, 1% sodium dodecyl sulfate, Tris buffer, NaCl, and EDTA, followed by phenol/chloroform extraction. RNA, 2.2 $\mu$g, enriched for messenger RNA, was isolated from 16 million cells with a Fast Track Kit Version 2.1 (Invitrogen Corp. San Diego, Calif.). RNA was denatured in formaldehyde, electrophoresed in a 1% agarose/formaldehyde gel, transferred to Schleicher & Schnell Nytran nylon membrane and cross-linked with ultraviolet light. The 1765 bp AAMP-1 cDNA was labeled with (alpha-$^{32}$P) dCTP (NEN Research Products, Boston, Mass.) using random priming. Hybridization overnight at 65° C. was performed according to Church and Gilbert (Proc. Natl. Acad. Sci 81, 1991 (1984)).
Figure 3:
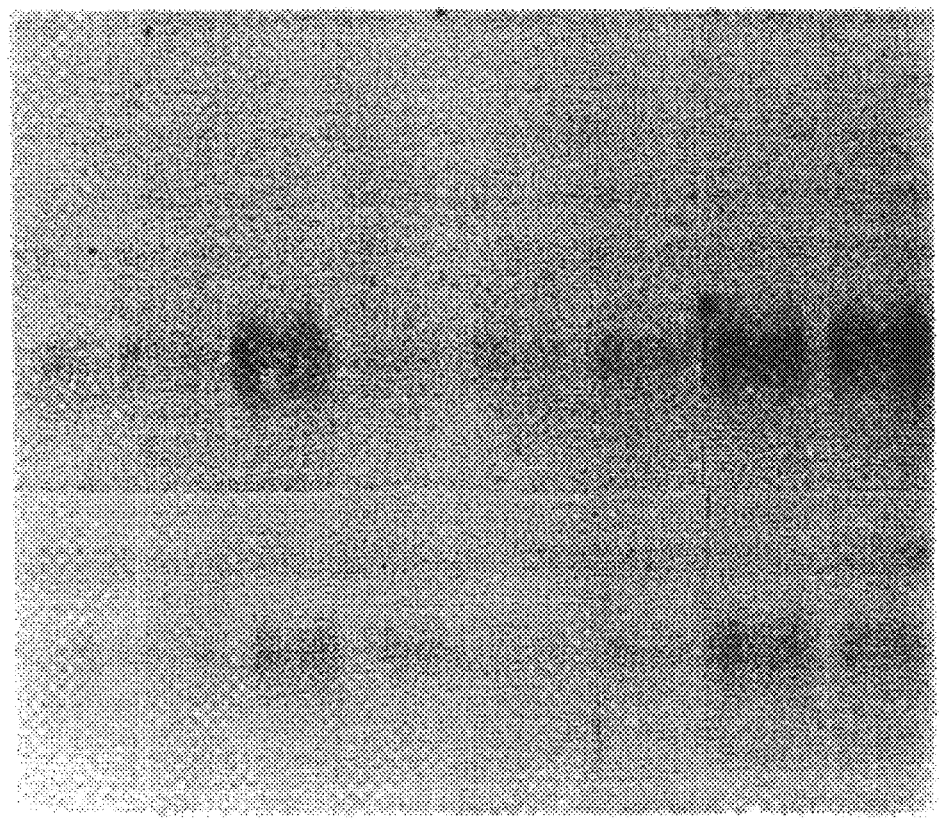
FIG. 3. Northern blot of AAMP-1 expression in human T-cell activation. Hours refer to time in culture. A: AAMP-1 single 1.6 Kb message. B: Beta-2 microglobulin standrd. Lanes 1–3: Non-stimulated human CD4+T cells Purity of the isolated cells was greater than 98%. Lanes 1 and 2 (0 and 24 hours, respectively) without mitogen stimulation, and lane 3 after 12 hours in the presence of the protein synthesis inhibitor, cycloheximide, which has been frequently observed to stabilize certain mRNA species (K. Kelly et al. P. Leder, *Cell* 35, 603 (1983)). Lanes 4–8: CD4+T cells activated with anti-CD3 and anti-CD2 monoclonal antibodies. Lanes 4, 5, 6, 7 and 8, represent the time points at 1, 2, 4, 16, and 24 hours, respectively. RNA samples were prepared from CD4+T cells by the guanidinium isothiocyanate-cesium chloride method of Maniatis et al. (T. E. Maniatis, E. F. Fritsch, J. Sambrook, *Molecular Cloning: A Laboratory Manual* (Cold Spring Harbor Laboratory, Cold Spring Harbor, New York, ed. 2, 1989), pp. 7.18–7.22.)). Ten micrograms of total RNA (each lane) electrophoresed in a formaldehyde/0.8% agarose gel was transferred to nitrocellulose and hybridized overnight, consecutively, at 42 C. to the (alpha-$^{32}$P) dCTP labeled, random primed probes, AAMP-1 and beta-2 microglobulin.

The term "AAMP" or "AAMP-1" refers to a protein or polypeptide which has a molecular weight of at least 45.7 kD, and is substantially or nearly homologous to the amino acid sequence shown in SEQ ID NO:7, variants, or fragments thereof. Ordinarily, such proteins will be at least about 50% homologous to the described amino acid sequence, preferably, in excess of 90% homologous, and more preferably at least about 95% homologous. Thus naturally occurring mammalian species, such as human variants of each, are included, as are other variants, analogues, and modified sequences. The proteins will ordinarily also exhibit at least some biological activity in common with AAMP or fragments thereof, e.g. heparin binding affinity, and cell adhesion properties. Closely related polypeptides or proteins retrieved by antisera are also included.

A polypeptide "fragment", "portion", or "segment" is a stretch of amino acid residues of at least about 6 amino acids, and more typically, at least about 12 amino acids.

The present invention embraces forms of AAMP protein or fragments thereof, which share the primary structure sequence, and is intended to encompass chemical and biochemical modifications, e.g., glycosylation, phosphorylation, ubiquitination, disulfide bonds, and other minor alterations in the basic primary sequence. In some embodiments, the modifications will be useful labeling reagents, or serve as purification targets, e.g., affinity ligands, as will be readily appreciated by those skilled in the art. A variety of methods for labeling polypeptides and of substituents or labels useful in labeling such polypeptides are well known in the art and include radioactive isotopes such as $^{32}$p, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are known in the art.

Such polypeptides will generally be soluble, but can be coupled to a solid phase support, e.g., nitrocellulose, nylon, column packing materials (e.g., Sepharose beads), magnetic beads, glass wool, cells, or other substrates, including but not limited to prosthetic devices (e.g., artificial heart valves), surgical materials (e.g. intravenous catheters, sutures) and the like.

The term "AAMP" when applied to a nucleic acid, refers to a nucleic acid which encodes an AAMP polypeptide or fragment thereof, and wherein said fragment is substantially or nearly homologous to the nucleotide sequence shown in SEQ ID NO:1, variants, or fragments thereof. The nucleic acids of the present invention include RNA, cDNA, genomic DNA, synthetic forms, and mixed polymers, both sense and antisense strands. Furthermore, different alleles of each isoform are also included. Recombinant nucleic acids comprising sequences otherwise not naturally occurring are also provided by this invention.

In a nucleic acid, a "fragment" or "segment" is a stretch of at least about 18 nucleotides, and usually at least about 36 nucleotides.

The terms "isolated", "substantially pure", and "substantially homogenous", are used interchangeably and describe AAMP protein or polypeptide, or fragments thereof, or a DNA segment encoding same, where such protein or peptide, or DNA molecule is separated from components that naturally accompany it.

An AAMP polypeptide or fragment thereof, or DNA segment encoding same is substantially free of naturally-associated components when it is separated from the native contaminants which accompany it in its natural state. Thus, a polypeptide that is chemically synthesized or synthesized in a cellular system different from the cell in which it naturally originates will be substantially free from its naturally-associated components. Similarly, a nucleic acid that is chemically synthesized or synthesized in a cellular system different from the cell in which it naturally originates will be substantially free from its naturally-associated components.

The term "homologous", when used to describe a nucleic acid, indicates that two nucleic acids, or designated sequences thereof, when optimally aligned and compared, are identical, with appropriate nucleotide insertions or deletions, in at least 60% of the nucleotides, usually from about 75% to 99%, and more preferably at least about 98 to 99% of the nucleotides.

Also included are, e.g, substantially similar sequences, allelic variations and natural or induced sequences. In addition, the present invention embraces chemically modified and substituted nucleic acids, e.g., those which incorporate modified nucleotide bases or which have been labelled. A wide variety of methods for modifying nucleic acids and various substituents are known in the art, and includes those as previously described for modifying peptides.

While the wild-type sequences of the alleles of the present invention will generally be employed, in some situations one or more mutations or minor modifications can be introduced, such as deletions, substitutions, inversions, or insertions resulting in changes to the amino acid sequence, providing silent mutations or modifying amino acid residues or amino or carboxy terminal groups.

The novel nucleic acids provided herein are useful for making large amounts of AAMP polypeptides, their fragments --,-- or nucleic acids, and their segments. A DNA segment encoding AAMP or fragments thereof will be used to prepare an expression construct by methods well known in the art. The expression construct normally comprises one or more DNA sequences encoding AAMP or fragments thereof, under the transcriptional control of a native or other promoter. Usually the promoter will be eukaryotic promoter for expression in a mammalian cell, wherein said mammalian cell may or may not, lack AAMP protein or fragments thereof. The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known (Sambrook, et al., Molecular Cloning: A Laboratory Manual (2d ed.), Vols. 1–3, Cold Spring Harbor Laboratory (1989)).

Conveniently available expression vectors can be employed, including the replication system and transcriptional and translational regulatory sequences together with the insertion site for the AAMP DNA sequence.

In cases where one wishes to expand the DNA sequence or produce the AAMP protein or fragments thereof in a prokaryotic host, a preferred promoter is a prokaryotic promoter, e.g., trp, lac, and lambda. Usually a strong promoter will be employed to provide for high level transcription expression.

A wide variety of hosts will be employed for expression of the AAMP protein or fragments thereof, both prokaryotic and eukaryotic. Useful hosts include bacteria, such as E. coli, yeast, filamentous fungi, insect cells, mammalian cells, typically immortalized, e.g., various mouse cell lines, monkey cell lines, Chinese hamster ovary cell lines, human cell lines, derivatives of them, or the like. In some cases, the cells will be derived from a neoplastic host cell or wild type cells will be transformed with oncogenes, tumor causing viruses or the like.

The means of introduction of the expression construct into a host cell will vary depending upon the particular construction and the target host.

Full length AAMP peptides or fragments thereof will be useful for producing antibodies, either polyclonal or monoclonal.

For monoclonal antibodies, appropriate animals are selected and the desired immunization protocol followed. After the appropriate period of time, the spleens of such animals are excised and individual spleen cells fused, typically to a immortalized myeloma cells under appropriate selection conditions. Thereafter the cells are clonally separated and the supernatants of each clone are tested for their production of an appropriate antibody specific for the desired region of the antigen. Techniques for producing antibodies are well known in the literature, see, e.g., Goding, et al., Monoclonal antibodies Principles and Practice (2d ed.) Academic Press, N.Y.; Harlow and Lane, Antibodies: A Laboratory Manual, Cold Spring Harbor Laboratory, New York (1988); and are exemplified by U.S. Pat. Nos. 4,381,292, 4,451,570 and 4,618,577. Other suitable techniques involve in vitro exposure of lymphocytes to the antigenic polypeptides or alternatively to selection of libraries of antibodies in phage similar vectors. (Huse, et al., Generation of a Large Combinatorial Library of the Immunoglobulin Repertoire in Phage Lambda, Science 246:1275–81 (1989). Monoclonal antibodies with affinities of 108 liters/mole, preferably $10^9$ to $10^{10}$ or stronger, will typically be made by these standard procedures.

The antibodies generated can be used for a number of purposes, e.g., in immunoassays, as probes, in diagnostics or therapeutics, or in basic studies seeking to dissect the portions of the protein responsible for the described properties of the protein or peptide or fragments thereof.

An immunological response is usually measured or detected with an immunoassay. Normally such immunoassays involve some purification of a source of antigen, for example, produced by the same cells and in the same fashion as the antigen being detected. The immunoassay will, in some instances, be a radioimmunoassay, an enzyme linked assay, a fluorescent assay, or any of many other choices, most of which are functionally equivalent but may exhibit advantages under specific conditions.

The antibodies of the present invention can be used with or without modification. Frequently, the antibodies will be labeled by joining, either covalently or non-covalently, a substance which provides for a detectable signal. A wide variety of labels and conjugation techniques are known and are reported extensively in both the patent and scientific literature. Suitable labels include radionucleotides, enzymes, substrates, cofactors, inhibitors, fluorescent moieties, chemiluminescent moieties, magnetic particles, and the like.

Proteins and peptides which promote cell-cell adhesion can be useful in promoting cell adhesion to a substrate, and thus promote tissue acceptance of prostheses, and also wound healing. Further, heparin binding polypeptides can also be used to concentrate heparin locally in tissues containing heparin, or to remove heparin from solutions containing heparin using such proteins or peptides as affinity ligands. Thus, AAMP and fragments thereof can also be used in promoting the above processes.

The quantities of agents necessary for effective therapy will depend upon many different factors, including means of administration, target site, physiological state of the patient, and other medicants administered. Thus, treatment dosages should be titrated to optimize safety and efficacy. These compounds can be administered to mammals for veterinary use and for clinical use in humans in a manner similar to other therapeutic agents, that is, in a physiologically acceptable carrier.

The pharmaceutical compositions will be administered by parenteral, topical, oral, or local administration, such as by aerosol, or transdermally, for prophylactic and/or therapeutic treatment. The pharmaceutical compositions can be administered in a variety of unit dosage forms depending upon the method of administration.

The pharmaceutical compositions of the present invention will often be administered intravenously. Thus, this invention provides compositions for intravenous administration which comprise a solution of the compounds of the present invention dissolved or suspended in an acceptable carrier, preferably an aqueous carrier. A variety of aqueous carriers can be used, e.g., water, buffered water, 0.4% saline, and the like. For solid compositions, conventional nontoxic solid carriers can be used which include, for example, pharmaceutical grades of mannitol, lactose, starch, magnesium stearate, sodium saccharin, talcum, cellulose. glucose, sucrose, magnesium carbonate, and the like.

Prostheses, surgical materials and the like, treated with the polypeptides of the present invention may be coated with a polypeptide composition, preferably wherein the polypeptide attaches to the surface of the material, and more preferably where the polypeptide is incorporated within the material.

As a diagnostic use, reagents provided herein can be used to detect and measure AAMP, and/or fragments thereof, or nucleic acids encoding for AAMP or fragments thereof in a target sample.

In detecting the presence of AAMP or nucleic acids encoding same, one would employ any of several methods well known in the art, including immunocrossreactivity, for AAMP, and Southern blots, Northern blots, plaque lifts, colony hybridization, or PCR or other amplification methods. See, e.g., Sambrook, et al, Molecular Cloning: A Laboratory Manual (2nd ed.), Vols. 1–3, Cold Spring Harbor Laboratory, (1989) and Current Protocols in Molecular Biology, F. Ausubel et al., ed. Greene Publishing and Wiley Interscience, New York (1987, and periodic updates), or, for PCR, e.g., U.S. Pat. Nos. 4,683,195, and 4,683,202, PCR technology, Erlich, ed., Stockton Press, New York (1989), and PCR Protocols: A Guide to Methods and Applications, Innis et al. eds., Academic Press, San Diego (1990).

More specific descriptions of the embodiments of the present invention are set out below.

In one embodiment, the present invention relates to a DNA segment coding for a polypeptide comprising an amino acid sequence corresponding to AAMP-1, or at least 6 contiguous amino acids thereof. In one preferred embodiment, the DNA segment comprises the sequence shown in SEQ ID NO:1, allelic or species variation thereof, or at least 18 contiguous nucleotides thereof (preferably, at least 18, 30, 40, or 50 contiguous nucleotides thereof). In a further preferred embodiment, the DNA segment encodes the amino acid sequence set forth in SEQ ID NO:7, allelic or species variation thereof, or at least 6 contiguous amino acids thereof (preferably, at least 6, 10, 15, 20, 30 or 50 contiguous amino acids thereof).

In a further embodiment, the present invention relates to a polypeptide free of proteins with which it is naturally associated or a polypeptide bound to a solid support and comprising an amino acid sequence corresponding to AAMP, or at least 6 contiguous amino acids thereof (preferably, at least 6, 10, 15, 20, 30 or 50 contiguous amino acids thereof). In one preferred embodiment, the polypeptide comprises the amino acid sequence set forth in SEQ ID NO:2, or allelic or species variation thereof equivalent thereto (for example, immunologically or functionally, equivalent thereto), or at least 6 contiguous amino acids thereof (preferably, at least 6, 10, 15, 20, 30 or 50 contiguous amino acids thereof).

In another embodiment, the present invention relates to a recombinant DNA molecule comprising a vector (for example plasmid or viral vector) and a DNA segment (as described above) coding for a polypeptide corresponding to AAMP-1, as described above. In a preferred embodiment, the encoding segment is present in the vector operably linked to a promoter.

In a further embodiment, the present invention relates to a cell containing the above described recombinant DNA molecule. Suitable host cells include procaryotes (such as bacteria, including *E. coli*) and both lower eucaryotes (for example yeast) and higher eucaryotes (for example, mammalian cells). Introduction of the recombinant molecule into the cell can be effected using methods known in the art.

In another embodiment, the present invention relates to a method of producing a polypeptide having an amino acid sequence corresponding to AAMP-1 comprising culturing the above-described cell under conditions such that the DNA segment is expressed and the polypeptide thereby produced and isolating the polypeptide.

In yet another embodiment, the present invention relates to an antibody having binding affinity for AAMP-1, or a unique portion thereof. In one preferred embodiment, AAMP-1 comprises the amino acid sequence set forth in SEQ ID NO:2, allelic or species variation thereof, or at least 5 contiguous amino acids thereof (preferably, at least 6, 10, 15, 20, 30 or 50 contiguous amino acids thereof). In one preferred embodiment, the antibody is 1AA3.

Antibodies (monoclonal or polyclonal) can be raised to AAMP-1, or unique fragments thereof, in its naturally occurring form and in its recombinant form. Binding fragments of such antibodies are also within the scope of the invention.

AAMP-1 may be joined to other materials, particularly polypeptides, as fused or covalently joined polypeptides to be used as immunogens. AAMP-1 or its fragments may be fused or covalently linked to a variety of immunogens, such as keyhole limpet hemocyanin, bovine serum albumin, tetanus toxoid, etc. See for example, Microbiology, Hoeber Medical Division (Harper and Row, 1969), Landsteiner, Specificity of Serological Reactions (Dover Publications, New York, 1962) and Williams et al., Methods in Immunology and Immunochemistry, Vol. 1 (Academic Press, New York, 1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., editors, Basic and Clinical Immunology, (Lange Medical Publications, Los Altos, CA, Fourth edition) and references cited therein, and in particular in Kohler and Milstein in Nature 256:495–497 (1975), which discusses one method of generating monoclonal antibodies.

In another embodiment, the present invention relates to a hybridoma which produces a monoclonal antibody or binding fragment thereof having binding affinity for AAMP-1 or fragments thereof. In one preferred embodiment, AAMP-1 has the amino acid sequence set forth in SEQ ID NO:2, allelic or species variation thereof, or at least 6 contiguous amino acids thereof (preferably, at least 6, 10, 15, 20, 30 or 50 contiguous amino acids thereof). In another preferred embodiment, the hybridoma comprises 1AA3.

In yet another embodiment, the present invention relates to a diagnostic kit comprising:
i) at least one of the above-described monoclonal antibodies, and
ii) a conjugate comprising a binding partner of said monoclonal antibody and a label.

In a further embodiment, the present invention relates to a diagnostic kit comprising a conjugate comprising:
i) at least one of the above-described monoclonal antibodies, and
ii) a label.

In a further embodiment, the present invention relates to a method of measuring the amount of AAMP-1 in a sample, comprising contacting the sample with the above-described antibodies and measuring the amount of immunocomplexes formed between the antibodies and any AAMP-1 in the sample. Methods of measuring the amount of immunocomplexes formed can be those well known in the art, such as RIA, ELISA, and direct and indirect immunoassays.

In another embodiment, the present invention relates to a therapeutic agent suitable for use in protecting against HIV infection or treating inflammatory immune or neoplastic disorders comprising the above-identified polypeptides in a quantity selected depending on the route of administration. Although subcutaneous or intramuscular routes of administration are preferred, the above described polypeptides could also be administered by an intraperitoneal or intravenous route. One skilled in the art will appreciate that the amounts to be administered for any particular treatment protocol can be readily determined. Suitable amounts might be expected to fall within the range of 1–50 micromoles.

In another embodiment, the present invention relates to a method of using the above described polypeptide to prevent AIDS. One skilled in the art will appreciate that the amounts to be administered for any particular treatment protocol can readily be determined.

In a further embodiment, the present invention relates to a DNA segment encoding a polypeptide, P189, derived from the amino-terminal region of AAMP. In a preferred embodiment the DNA segment has the nucleotide sequence shown in SEQ ID NO:3, or a fragment thereof. In a further preferred embodiment, the DNA segment has the nucleotide sequence shown in SEQ ID NO:5.

In another embodiment, the present invention relates to a polypeptide derived from the amino-terminal region of AAMP. In a preferred embodiment, the polypeptide is P189, and contains the amino acid sequence shown in SEQ ID NO:4, or a fragment thereof. In another preferred embodiment, the polypeptide has the amino acid sequence shown in SEQ ID NO:6.

In an additional embodiment, the present invention also relates to the above described P189 polypeptide or a fragment thereof, bound to a solid support.

A further embodiment of the present invention relates to a recombinant DNA molecule comprising a vector and a DNA segment encoding the human cell adhesion polypeptide, P189. In a preferred embodiment, the DNA segment has the nucleotide sequence shown in SEQ ID NO:3. In yet another preferred embodiment, the DNA segment has the nucleotide sequence shown in SEQ ID NO:5.

In another embodiment, the present invention relates to a cell containing the above recombinant DNA molecule and capable of expressing an adhesion polypeptide having the amino acid sequence shown in SEQ ID NO:4.

In a further embodiment, the present invention also relates to a method of promoting cell-cell adhesion by introducing into a cell culture an effective amount of an adhesion polypeptide selected from the group consisting of AAMP, P189, and fragments thereof.

In another embodiment, the present invention relates to a method of promoting cellular attachment to a substrate, by treating the substrate with an adhesion polypeptide selected from the group consisting of AAMP, P189, and fragments thereof. In a preferred embodiment, the substrate comprises a prosthetic device, whereby said method promotes acceptance of the prosthetic device. One skilled in the art will appreciate that the amounts to be administered for any particular treatment protocol can be readily determined depending upon the level of cellular attachment desired.

In a further embodiment, the present invention relates to a method for promoting the healing of wounds in a patient by administering to said patient an effective amount of an adhesion polypeptide selected from the group consisting of AAMP, P189, and fragments thereof. Again, one skilled in the art will appreciate that the amounts to be administered for any particular treatment protocol can be readily determined either by analogy to other heparin binding peptides known in the art, or by other methods known in the art. See, e.g., U.S. Pat. No. 5,081,031 to Furcht et al., U.S. Pat. No. 5,152,784, to Tsilibary et al., U.S. Pat. No. 5,120,828, to Charonis.

In still another embodiment, the present invention relates to a method for concentrating heparin locally, in tissues by administering an effective amount of an adhesion polypeptide capable of binding heparin, to the area where heparin concentration is desired, wherein said adhesion polypeptide is selected from the group consisting of AAMP, P189, and fragments thereof. In a preferred embodiment, the method is used to concentrate heparin around foreign material by coating said foreign material with an adhesion polypeptide selected from the group consisting of AAMP, P189, and fragments thereof. One skilled in the art will appreciate that the amounts to be administered for any particular treatment protocol can be readily determined either by analogy to other heparin binding peptides known in the art, or by other methods known in the art.

The present invention is described in further detail in the following non-limiting Examples.

EXAMPLES

The following protocols and experimental details are referenced in the Examples that follow:

Cells.

Human peripheral blood mononuclear cells (PBMC) from normal donors were separated by Ficoll-Hypaque density-gradient centrifugation. Resting CD4+T lymphocytes were subsequently obtained by rigorous immunomagnetic negative selection with Advanced Magnetic Particles (Advanced Magnetic, Cambridge, MA) or Dynabeads™ particles (Dynal Inc., Fort Lee, N.J.) both bound to goat anti-mouse IgG. Negative selection was performed as described (Horgan, K. J. and Shaw, S., Immuno-magnetic negative selection of lymphocyte subsets in Coligan, J.E. et al. (Eds.) Current Protocols in Immunology, Wiley Interscience, New York (1991) p. 7.4.1.) using a cocktail of mAbs consisting of anti-HLA class II mAb (IVA12), CD20 mAb (1F5), CD16 mAb (3G8) CD11b mAb (NIH11b-1), CD14 mAb (MMA), CD8 mAb (B9.8), and mAb against glycophorin (10F7). Purity of the isolated cells was more than 98%. The selected CD4+T-cells were free of monocytes based on the criterion that there be no proliferative response to optimal concentrations (1/200 dilution) of Phytohemagglutinin (M form) (PHA) (GIBCO, Grand Island, N.Y.) (Davis, L., and P. E. Lipsky (1986) J. Immunol. 136:3588).

T-cell Activation Assays.

T-cell activation assays were performed using standard techniques. Briefly $10\times10^6$ purified CD4+T-cells were cultured in 35 mm flat bottom wells for various time periods in culture medium [RPMI 1640 (Hazleton Biologics Inc. Lenexa, KS) supplemented with 20 mM glutamine (Hazleton), 10% heat inactivated FCS (Biofluids, Rockville, Md.), 100 IU/ml of penicillin, and 100 $\mu$g/ml streptomycin)], either unstimulated or stimulated with antibodies bound to the wells. T-cell stimulatory conditions were as described (van Seventer, G. A. et al. (1991) Eur. J. Immunol. 21:1711). mAbs were immobilized on the plastic of the well by dilution in PBS and overnight incubation at 4° C., followed by washing with PBS. The CD3 mAb OKT3 and the CD2 mAb 95-5-49 were applied at 1 $\mu$g and 10 $\mu$g purified Ig/ml respectively, all in a volume of 3 ml/well. The following monoclonclantibodies were used as purified immunoglobulin derived from ascites fluid; CD2 mAb (directed against the T11.1 epitope): 95-5-49, IgG1 (hybridoma kindly provided by Dr. R. R. Quinones, George Washington University, Washington, D.C.); CD3 mAb OKT3, IgG2a (ATCC, Rockville, Md.). Cycloheximide, when present, was used at a concentration of 10 $\mu$g/ml.

CD4+T Cell RNA Preparation.

RNA samples were prepared from CD4+T cells by the guanidinium isothiocyanate-CsCl method of Maniatis et al. (Maniatis, T. E. et al. (1989) Molecular cloning: a laboratory manual. 2nd Edition. Cold Spring Harbor Laboratory, Cold Spring Harbor, N.Y.). 10 $\mu$g of total RNA was resolved for each condition on a formaldehyde 0.8% agarose gel, transferred to nitrocellulose, and hybridized at 42° C. to $^{32}$P-labeled purified AAMP-1 CDNA insert prepared by random priming.

Antibody Preparation.

The adaptive passive transfer technique in Balb/c mice utilizing whole cells from the human melanoma A2058 cell line as antigen was used to generate hybridomas with myeloma cells. Selection of the 1AA3 clone was based on its inhibition of motility when assayed in modified Boyden chambers described previously (Stracke, M. L. et al. (1987) Biochem. Biophys. Res. Comm. 146, 339–345) using gelatin coated filters and various chemoattractants (collagen type IV, laminin, autocrine motility factor, fibronectin, and insulin-like growth factor I. The clone 1AA3 was recloned by limiting dilution to produce the 1AA3AA clone.

cDNA Library and Screening.

The human melanoma A2058 cDNA expression library was constructed in the lambda gt11 vector by Clontech Laboratories, Inc. Y1090 Escherichia coli infected by the phage were plated and blotted onto nitrocellulose filters (Schleicher & Schnell) for immunoassay with 1AA3AA antibody. Reactive plaques were detected using peroxidase-coupled antibody specific for mouse IgG.

Northern Blotting. Preparation of A2058 human melanoma RNA enriched for messenger RNA was isolated with a Fast Track Kit Version 2.1 (Invitrogen Corp). Total cytoplasmic RNA was isolated according to a published method (Gough, N. M. (1988) Anal. Biochem. 173, 93–95) by suspending 4 ml cells on ice with 0.8ml chilled Solution A (10 mM Tris Cl, pH 7.5, 0.15 MNaCl, 1.5 mM Mgcl$_2$, and 0.65% Nonidet P-40). The supernate, obtained after vortexing and centrifuging (800×G, 5 min, 4° C.) was mixed with 0.8 ml Solution B (7M Urea, 1% SDS, 0.35 M NaCl, 10 mM EDTA, pH 8.0, and 10 mM Tris Cl, pH 7.5) and 1.6 ml. Solution C (phenol: chloroform: isoamyl alcohol (50:50:1). RNA was removed in the aqueous phase and ethanol precipitated.

RNA was denatured in formaldehyde, separated on a 1% agarose/formaldehyde gel (Sambrook, J. et al. (1989) Molecular Cloning: A Laboratory Manual, Cold Spring Harbor Laboratory, Cold Spring Harbor, NY) and transferred overnight to S&S Nytran (Schleicher & Schnell) and crosslinked to it with ultraviolet light in the Stratalinker apparatus (Stratagene). The 1766 bp CDNA insert labeled with ($\alpha$-$^{32}$P)dCTP (NEN Research Products) with the Random Primer DNA Labeling System (Bethesda Research Laboratories, Life Technologies, Inc.) was used as probe.

Northern blots for total A2058 melanoma cytoplasmic RNA and RNA enriched for messenger RNA were performed with the Church protocol (Church, G. and Gilbert, W. (1984) Proc. Natl. Acad. Sci 81, 1991). The filter was washed at 65° C. for 20 minutes with wash buffer (1% sodium dodecyl sulfate, 40 mM NaH$_2$PO$_4$, 1 mM EDTA) three times and then autoradiographed at −70° C.

DNA Sequencing.

Positive phage inserts were subcloned into Bluescript plasmid (phagemid) (Stratagene) for production of DNA for sequencing. Double-stranded cDNA was sequenced using the dideoxynucleotide chain termination method with Sequenase (United States Biochemical). Sequence obtained with the SK primer (Stratagene) specific for the adjacent Bluescript vector region was determined first. Subsequent sequencing utilized primers prepared on site based on previously obtained sequence for both strands completely.

Seguence Data Analysis.

GenBank (Intelligenetics, Inc.) was searched with the program and further analyses of the sequence was accomplished with the following computer programs and software: RAOARGOS (a program for locating transmembrane regions), PESTFIND (a program for locating degradable protein sites), PROSITE (a program for locating consensus sequences in the protein), AACLUST (a program for locating similarly charged amino acids), KERMIT (a communications software), NALIGN (a nucleic acids aligning program), PALIGN (an amino acid sequence aligning software), REPEATS (a program for detecting repeats in the amino acid sequence), SEQIN (an editing program for sequences), TRANSL (a program for translating a nucleic acid sequence to an amino acid sequence), and DIAPRO (a program for defining the secondary structure of an amino acid sequence). These programs are included in PC/Gene (Intelligenetics, Inc.). The NBRF protein sequence data base from the Protein Identification Resource National Biomedical Research Foundation (NBRF) was searched with the PQS, XQS, and NEW programs and other programs were used for sequence analyses. In the ALIGN program, sequences are matched with a bias and gap penalty, scored in a matrix, scrambled and rescored many times to yield a mean best random score and standard deviation (SD). The score for the real sequences is expressed as the number of SD units away from the random mean score (Dayhoff, M. O. et al. (1983) Meth. Enzym. 91, 524–545). All of our alignments were done with the Mutation Data Matrix (250 PAMs), md, a bias of 6, a gap penalty of 6 and 150 random runs (Williams, A. F. and Barclay, A.N. (1988) Ann. Rev. Immunol. 6, 381–405).

EXAMPLE 1

Characterization of AAMP-1

AAMP-1 Antibodies.

The monoclonal antibody produced against AAMP-1 is of the IgG-I subtype. It cryoprecipitates and loses activity with freezing and purification methods that require precipitation. Initial results indicated that this antibody inhibited adhesion and motility of A2058 melanoma cells in chemoattractant assays performed with the modified Boyden chamber. However, the inhibition occurred in an all or none fashion without a reliable dose response curve and steric hindrance due to self aggregation of the antibody cannot be ruled out at this time.

Characterization of the Proteins Identified by 1AA3AA Antibody.

A2058 melanoma cell surface immunofluorescent staining has been seen with 1AA3AA. It identifies a protein on A2058 whole cell lysate immunoblots with a molecular weight of approximately 95 kD that shows an apparent slight increase with reduction to 105 kD.

The betagalactosidase fusion protein shows positive staining with the 1AA3AA antibody on immunoblots. The predicted AAMP-1 protein is described below. Its molecular weight and glycosylation potential are not consistent with the protein identified by 1AA3AA described above.

Isolation of 1AA3AA Positive cDNA Clones.

Initial screening of phage plaques yielded three positive clones similar in size, identified as 1AA34A, 1AA335A, and AAMP-1. They all cross hybridized with each other on dot blots. AAMP-1 was slightly larger (less than 10 bp different) and was chosen for sequencing.

Northern Blot of A2058 Melanoma Total Cytoplasmic and Polyadenylate Enriched RNA.

When all three positive clones were used to probe a blot of total cytoplasmic A2058 RNA they hybridized with only one band. A single band at 1.6 kb is seen on a blot of both total cytoplasmic and polyadenylate enriched A2058 RNA probed with AAMP-1 in FIG. 1.

Nucleotide Seguence.

The AAMP-1 cDNA has 1765 bp with the longest open reading frame (1278 bp) occurring in the second reading frame of the sequence (FIG. 1; SEQ ID NO:7). 67% of the sequence excluding the poly A tail is involved with repeats that include 7 or more nucleotides each. The largest direct repeat is A G G A G G A A G A G (shown in SEQ ID NO: 8)at nucleotides #200 and #1684. Its sequence overlaps with that of a ten member repeat at nucleotides #196 and #1427. Another ten member direct repeat occurs at positions #947 and #1507 and a third 10 member repeat is at #1110 and #1170. Several palindromes exist in the sequence. The longest palindrome G G G T T C T A G A A C C C (shown in SEQ ID NO: 9)occurs at nucleotide #227. Ten member palindromes also occur at nucleotides #1148 and #1341. Eight member palindromes are present at nucleotides #227, #1118, #1514, and #1709. The last 25 nucleotides of the 1765 bp sequence comprise the polyadenylated nucleotide tail and the consensus sequence A A T A A A A that commonly precedes a poly A tail is present at nucleotide #1722.

Predicted Amino Acid Sequence.

The 1278 bp open reading frame in AAMP-1 CDNA predicts a protein with a molecular weight of at least 45.7 kilodaltons.

The predicted protein contains multiple immunoglobulin-like domains qualifying it as a member of the immunoglobulin (Ig) superfamily. It contains two potential transmembrane regions and several serine/threonine phosphorylation sites. An acidic amino terminal region is also present. A heparin binding site is present at aa 7–12. This region is included in both P189 and its fragment (See SEQ ID NO:4 and SEQ ID NO:6, respectively)

Immunoglobulin Superfamily Homology.

Comparison of AAMP's sequence with protein databanks indicates that it is unique and contains immunoglobulin-like domains. The Ig type domains in AAMP show sequence homologies with multiple Ig domains of known family members (indicated by scores in the ALIGN program of Dayhoff et al., Meth. Enzym. 91:524–45 (1983) greater than 3.00 S.D.) The AAMP region, aa 87–357, encompassing all potential Ig domains, contains predicted beta sheets and turns as secondary structure using the method of Chou and Fasman (*Advances in Enz.* 47, 45 (1978)) in the NRBF program, CHOFAS, consistent with the characteristic secondary structure of Ig domains (FIG. 1) (Williams et al., Ann. Rev. Immunol. 6:381–405 (1988); Williams et al., in Immunoglobulin Genes (Honjo, T., Alt, F. W., and Rabbitts, T. H., eds.) pp361–87, Academic Press Limited, San Diego, Calif.). Four potential Ig domains formed around non-overlapping cysteine pairs, are possible from these predictions, but this arrangement only allows a small number of amino acid residues between cysteines of some of the neighboring domains. Therefore, alignments with Ig superfamily members were performed allowing for the short distances between the putative domains so that neighboring AAMP domains were excluded. This designation of domains in AAMP yielded the largest possible number of Ig superfamily relatives and significant alignments with multiple domains in some proteins, such as, DCC protein Fearon et al., Science 247:49–56 (1990)), neural-glial cell adhesion molecule (Burgoon et al., J. Cell Biol. 112:1017–29 (1991)), and NCAM (Cunningham et al., Science 236:799–806 (1987)). Other designations of potential domains defined by different cysteine pairs yielded fewer matches.

Potential Transmembrane Regions.

AAMP has one transmembrane region lacking charged residues and another containing aspartic acid as predicted according to the method of Rao and Argos (Rao, et al., Biochem. Biophys. Acta 869:197–214 (1986) using the ROAARGOS program, PC/Gene (1991) Intelligenetics, Inc., Release 6.5. The uncharged and more likely transmembrane region, aa385–410, of AAMP also aligns with CD4's transmembrane region.

Potential Phosphorylation Sites.

On the amino terminal side of the AAMP-1 TMRs there are five sites that have the consensus pattern for potential casein kinase II phosphorylation sites, (S,T)-x-x-(E,D). These involve serines at positions #14, #133, and #319 and threonines at positions #120 and #176 (shown in SEQ ID NO:7).

Four potential protein kinase C phosphorylation sites are also present with the consensus pattern of (S,T)-x-(R,K). These include two threonines at positions #249 and #302 on the amino terminal side of the TMR and a threonine at position #369 and a serine at position #419 (shown in SEQ ID NO:7) on the carboxy terminal side of the TMR.

EXAMPLE 2

Peptide Preparation

Peptide P189, derived from the amino terminal of the AAMP sequence, and variants of peptide P189 (The specific peptides and sequences are as follows: P350-scrambled sequence of P189 (shown in SEQ ID NO:10), P357-QQLQQMESESES (shown in SEQ ID NO:11), P358-RRLRRMQSQSQS (shown in SEQ ID NO:12), P359-RRGRRGESESES (shown in SEQ ID NO:13), P360-RRLRRMEAEAEA (shown in SEQ ID NO:14), P369-RLRRMESESE (shown in SEQ ID NO:15), were synthesized on a Biosearch model 9600 peptide synthesizer using standard Merrifield solid phase synthesis protocols, and t-butoxycarbonyl chemistry. The peptides were analyzed by reverse phase high performance liquid chromatography.

Cell Adhesion Assays

Specific adhesion of A2058 human melanoma cells to AAMP peptides attached via linker arms to plates was performed according to known methods with changes where stated. The peptides were first solubilized at a concentration of 2 mg/mL in a 50% DMSO solution with heating to 100° C. for 10 minutes and were then spun at 12000 g for 1 minute to remove any residual particulates. Peptide aliquots, 0.25 mL, combined with 4.75 mL of sulfo-N-hydroxysuccinimide solutions (184 ug/mL) (Pierce) were added to CovaLink™ 96 well plates (Nunc) which are provided from the manufacturer with amino groups attached 2 nm above the plate surfaces via linker arms at a density of $10^4/cm^2$. Appropriate dilutions with final volumes of 50 uL of the peptide-sulfo-N-hydroxysuccinimide solution were prepared for each peptide in duplicate for each assay. 1-Ethyl-3-(3-dimethylaminopropyl)-carbodiimide (1.23 mg/mL) (Sigma) was added as 50 uL aliquots to each well for a 2 hour incubation at room temperature resulting in attachment of peptides to the linker arms which allows their complete sequences to be available for binding to cell surfaces. Washing 3 times with modified CovaLink™ Buffer (116.9 g/L NaCl, 10.0 g/L $MgSO_4$, 0.05% Tween 20) removed the reagents. The plates were left in the third wash overnight and were then washed a fourth time with CovaLink Buffer containing PBS. For the heparin binding inhibition assays the fourth wash also included the designated concentration of LYPHOMED™heparin sodium which was left on the plates for one hour at room temperature. In these assays, the plates were washed again twice to remove unattached heparin before cells (100,000/well) were added. Following one hour incubations at 37° C., unattached cells were rinsed away in PBS and the attached cells were stained with Diff Quik™ (Baxter Healthcare). Stain was eluted with 10% methanol and 5% acetic acid solution and read in a spectrophotometer at 620 nm. Cellular dye retention, measured spectrophotometrically at 620 nm, was linearly related to the number of cells bound (visual counts) over the range of absorbances obtained. One O.D. unit represented approximately 100,000 attached melanoma cells (101,679+/−11,800 S.D., actual cell count). The student t test was used to test for differences between the means of the cell binding results for peptides of the invention and control peptides.

Figure 5:
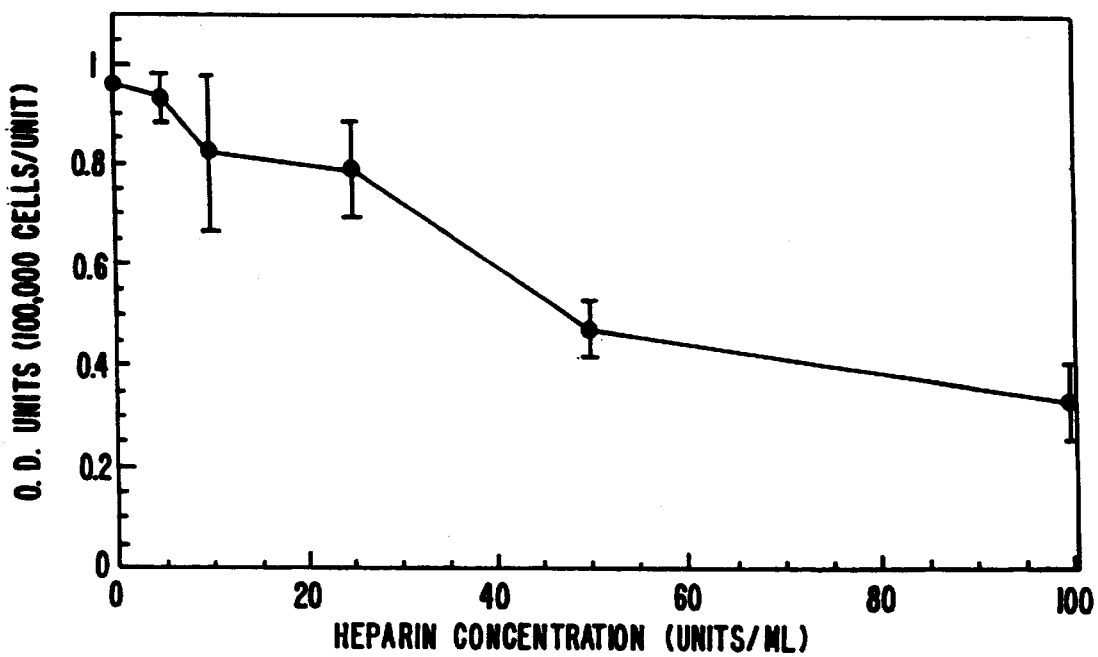
FIG. 5. Heparin inhibition of cell adhesion to immobilized P189 peptide. Solubilized P189 was added to wells of CovaLink™ plates covered with amino groups on linker arms that attach peptides so that their complete sequences are available for binding to ligands or cells. Increasing concentrations of heparin as indicated along the X-axis were added in wash solutions following peptide linkage to the plates. Unbound heparin was washed away prior to the addition of A2058 melanoma cell suspensions. Following a one hour 37° C. incubation, unbound cells were washed away and the remaining cells were Diff Quik™ stained™. Dye retention in the attached cells was quantified spectrophotometrically following solubilization. Each O.D. unit represents approximately 100,000 cells. A control peptide, P350, created from the scrambled sequence of P189, showed 50% less cell binding with no exposure to heparin and 30% more cell binding following the maximum heparin exposure shown for P189.

Results for studies of cell binding on CovaLink™ plates were obtained for P189, and peptides containing variants of the P189 sequence. Peptides P189, and the sequence variants which contain the Arg Arg X Arg Arg X motif (where X=Leu, Met, or Gly) at 7.2 uM all showed comparable cell binding results: P189=0.708+/−0.104 S.D., P358=0.710+/−0.013 S.D., P359=0.670+/−0.046 S.D., P360=0.645+/−0.60 S.D. units O.D., of adherent cells dye retention. Each O.D. unit represents approximately 100,000 attached cells. the peptides lacking the Arg Arg X Arg Arg X motif exhibited significantly lower cell binding properties (FIG. 5). In half-strength DMEM (diluted with PBS) with 0.1% BSA, the difference between P189's binding and that of P350 (the scrambled version of P189) increased so that P189's binding was 2.06 times that of P350. Heparin at increasing concentrations progressively inhibited cell binding to P189 (as shown in FIG. 5). Cell binding to P189 coated plates previously incubated with heparin at 50 U/mL was reduced to 49% of the cell binding to P189 plates that were never exposed to heparin. With 100 U/mL of heparin, the cell binding fell further and was 30% less than cell binding to the scrambled peptide (P350).

Cell Aggregation Assays

Tissue culture chamber slides (8 chamber Permanox™ slides, Lab Tek™, Nunc Inc.) were coated (1 ug/mL) with mouse Type IV collagen (Collaborative Biomedical products). The Type IV collagen solution was aspirated after one hour at room temperature and the slides were allowed to air dry. Single cell suspensions of A2058 human melanoma cells in 0.1% BSA-DMEM (0.5 million/mL) were incubated separately with peptides, P189 and variants, one hour at room temperature on a rocker. Aliquots of the cell suspensions (250 uL) were then pipetted into slide chambers with duplicates for each data point. The slides were incubated in na petri dish at 37° C. for 1 hour and were then gently washed in PBS and stained with Diff Quik. They were microscopically evaluated for the number of large cell groups (>10 rounded, tightly clustered cells). Additional assays were performed to check for effects of additives on cell aggregation induced by P189 (200 ug/mL). These included heparin sodium (5–25 U/mL), sodium oxamate (0.03–0.1 M), cycloheximide (1–10 ug/mL)(Sigma), methyl-alpha-D-mannopyranoside (0.06 M) (Calbiochem Corp.), D(+)-galactose, N-acetyl-D-glucosamine (0.06 M)(Sigma Chemical).

Figure 4:
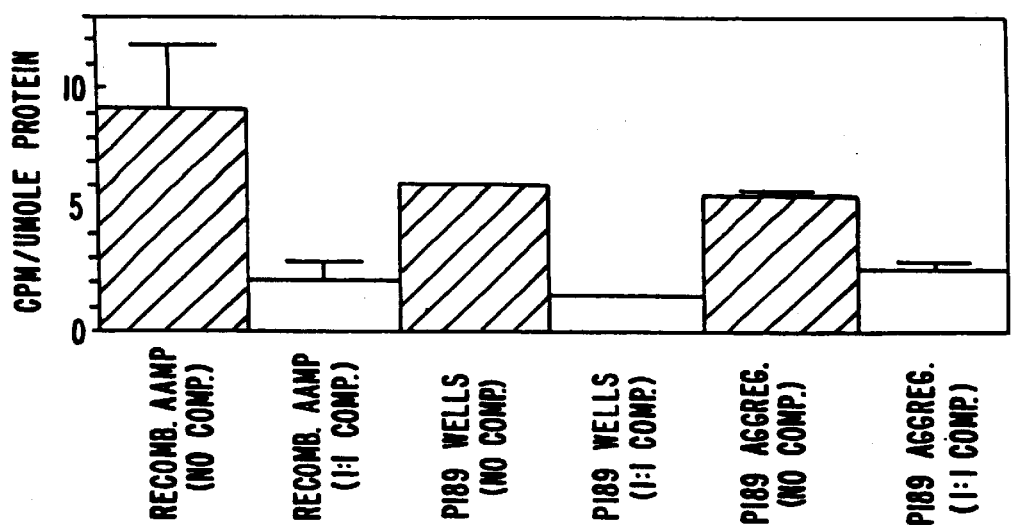
FIG. 4. AAMP heparin binding. Recombinant AAMP protein, approximately 15 ug gel-purified and blotted onto Immobilon-P™, binds tritiated heparin (2.5 U/mL) 2.2+/−0.4 times more than background (BSA) and is expressed as counts per minute (cpm), above background per mole of protein (6 assays) and is competed with an equal amount of unlabeled heparin (3 assays). The peptide derived from AAMP, P189, 0.3 ug per CovaLink™ plastic well (2–3 per data point), binds tritiated heparin (50 U/mL) 3.0+/−0.6 times more than background (wells treated with same buffers including 0.1% BSA) in two assays; in the assay with maximal peptide binding, the results in cpm/umole protein shown below (for tritiated heparin binding both without, and with 1:1 cold heparin competition) approach the values for the recombinant AAMP protein. P189 aggregates precipitated from 200 ug/mL solutions in polypropylene tubes, bind tritiated heparin (0.05 U/mL) 9.1+/−1.3 times more than background (rinse from tube incubated with same buffers including 0.1% BSA) with results (shown) that are also in the same range as those for the recombinant protein (2 assays). Its binding can also be competed with unlabeled heparin (1:1). Background binding in assays of recombinant AAMP competed with unlabeled heparin were standardized to AAMP recombinant protein's average background. Recovery of tritiated heparin was 18% and 25% in P189 aggregate binding assays. (Recomb.=recombinant, Comp.=competition).
Figure 6:
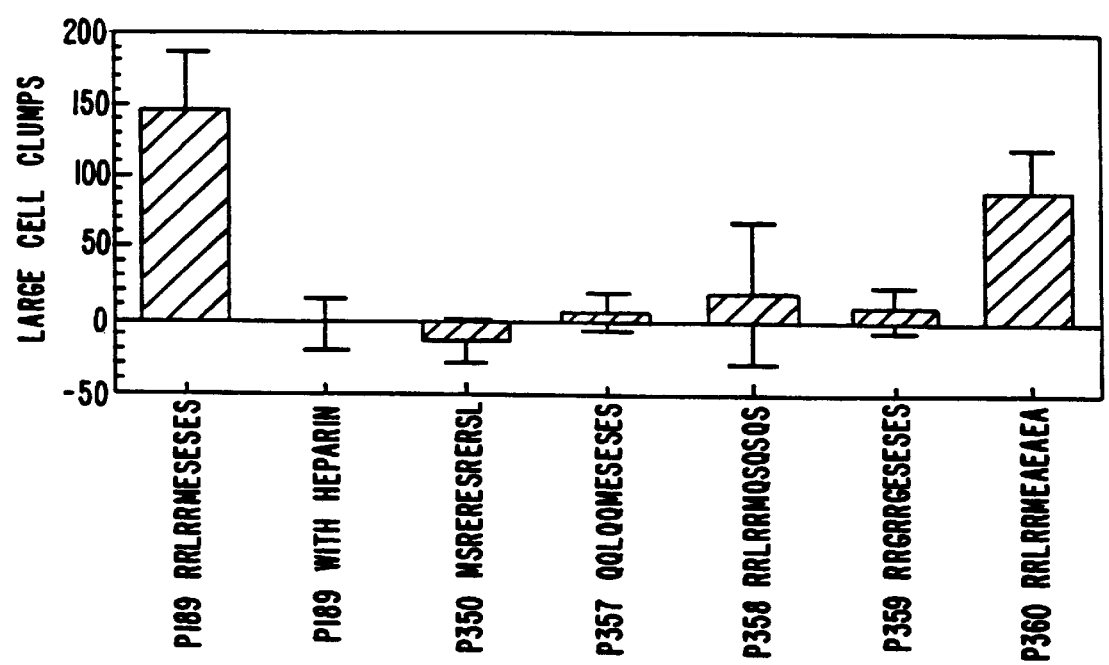
FIG. 6. Peptide induced aggregation of A2058 melanoma cells. Visual counts of the cell aggregates formed in cell/peptide suspensions and allowed to settle on slides. Aggregates of 10 or more rounded tightly clustered cells were counted in the central 140 mm$^2$ areas of the chamber regions on the slides for each peptide (multiple slides, with correction for background clumping on the same slide with no peptide present). Heparin (5 U/mL), abolished P189's aggregating effects on cells.

P189, 200 ug/mL, forms aggregates in solution that also bind tritiated heparin (0.05 U/mL) above background levels (9.1+/−1.3 X, in 2 assays) with a 55% reduction in counts in the presence of an equal amount of unlabeled heparin. The average binding above background was 5567+/−189 cpm/umole protein with no competition and 2495+/−320 cpm/umole protein with unlabeled heparin present (1:1 competition) (FIG. 4). P189 also aggregated A2058 melanoma cells resulting in numerous, tightly clustered groups of 10 or more cells. P350 (P189's scrambled version) showed no effect on A2058 melanoma cell aggregation and heparin, 5U/mL, totally abolished the cell aggregating effects of P189. Other peptides with variant sequences (P357–P360) showed much smaller effects on cell aggregation (FIG. 6). The two peptides having the Arg Arg Leu Arg Arg Met sequence motif (P358 and P360), bound cells more than the other variants lacking this motif, but did not bind cells as well as P189. The cell aggregation caused by P189 was not eliminated by treatment of the cells with inhibitors of glycolysis and protein synthesis, or by sugars including methylmannopyranoside, galactose, N-acetyl-glucosamine, and lactose.

$H^3$-Heparin Binding Assays.

Heparin binding assays utilizing competition of tritiated heparin (heparin sodium salt, [$^3$H(G)]-, NEN DuPont), with unlabeled heparin, were performed for recombinant AAMP, solubilized P189 (immobilized on CovaLink™ plates), and for aggregated P189 in 0.1% BSA-DMEM solutions. Recombinant AAMP in bacterial lysate and bovine serum albumin in equal amounts were electrophoresed for gel purification, and blotted onto Immobilon-P™. These blots were incubated 3 hours with tritiated heparin, 2.5 U/mL (10.7 uCi/mL) at room temperature, alone and with increasing amounts of unlabeled heparin (0.125–0.25 U/mL) for competition. Following 3 washes, the bands of AAMP recombinant protein and BSA (triplicates for each heparin concentration) were cut from the blotted Immobilon P strips, placed in scintillation vials, and counted for comparisons. Solubilized P189 (6.25 ug/mL) was immobilized on CovaLink™ plates, as described previously, and incubated one hour at room temperature with tritiated heparin, 50 U/mL (0.213 uCi/mL), alone and with increasing amounts of unlabeled heparin (50–500 U/mL) for competition. Following three washes, the plate wells, in duplicates or triplicates for each heparin concentration, were placed in scintillation vials and counted. In separate assays, aggregates of P189 (200 ug/mL in 0.1% BSA-DMEM) were incubated one hour on a rocker at room temperature with tritiated heparin (0.05 U/mL) alone and with increasing amounts of unlabeled heparin (0.05–5 U/mL) for competition. Following centrifugation, the precipitate was washed with 0.1% BSA-DMEM, centrifuged again, and then transferred to scintillation vials for counting. The background cpm/umole protein levels for assays with AAMP recombinant protein competed with unlabeled heparin, were standardized to AAMP recombinant protein's average background cpm/umole protein with no labeled heparin present.

Heparin Binding of AAMP and P189.

Recombinant AAMP, gel purified from bacterial lysate and blotted onto Immobilon-P™, binds heparin when compared with an equal amount of bovine serum albumin blotted under the same conditions. AAMP's binding of tritiated heparin (2.5 U/mL) can be competitively inhibited by an equal amount of unlabeled heparin (FIG. 4). Binding of tritiated heparin by AAMP recombinant protein is expressed as cpm above background per umole protein for binding without (9134+/−2699 S.D. cpm/umole protein, 6 assays) and with competition by an equal amount of cold heparin (2139 cpm+/−762 S.D. cpm/umole protein, 3 assays).

Solubilized P189 (6.25 ug/mL) covalently attached to CovaLink™ plates, binds heparin as indicated by binding above background (3.0+/−0.6 times) in 2 assays and a reduction when tritiated heparin (50 U/mL) binding is competed by an equal amount of unlabeled heparin (FIG. 4). In the best assay, the tritiated heparin binding with no competition yielded 6035 cpm/umole protein that was competed to 1423 cpm/umole protein with an equal amount of unlabeled heparin.

AAMP, and its fragments exhibit the ability to promote cell-cell, and cell-substrate adhesion. These peptides also exhibit heparin binding capabilities. Such properties have proven useful in promoting wound healing, prosthetic acceptance, and heparin concentration in tissue, as well as inhibiting metastasis and invasion of malignant cells.

All publications, patent applications, and patents mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A substantially pure polypeptide comprising an amino acid sequence showing at least 90% sequence identity to SEQ ID NO. 7, or a fragment thereof, wherein the polypeptide or fragment is capable of binding to heparin.

2. A substantially pure polyepeptide comprising the amino acid sequence of SEQ ID NO. 7.

3. The substantially pure polypeptide of claim 1 comprising the amino acid sequence of SEQ ID No:7 or an allelic or species variant thereof.

4. The substantially pure polypeptide of claim 1 bound to a solid support.

* * * * *